United States Patent [19]

Patel

[11] 4,269,668

[45] May 26, 1981

[54] EXTRACTIVE DISTILLATION OF C-4 HYDROCARBONS USING MODIFIED ALKOXYNITRILE SOLVENT

[75] Inventor: Pradeep V. Patel, Parma, Ohio

[73] Assignee: The B. F. Goodrich Company, Akron, Ohio

[21] Appl. No.: 151,011

[22] Filed: May 19, 1980

[51] Int. Cl.$^3$ ............................ B01D 3/40; C07C 7/08
[52] U.S. Cl. ............................................ 203/9; 203/51; 203/53; 203/57; 203/58; 203/60; 203/65; 203/84; 252/364; 585/810; 585/833; 585/864; 585/865; 585/950
[58] Field of Search .................... 203/9, 8, 51, 53, 57, 203/58, 60, 65, 84; 252/364; 585/810, 800, 833, 837, 834, 860, 864, 865, 950

[56] References Cited

U.S. PATENT DOCUMENTS

| | | | |
|---|---|---|---|
| 3,515,762 | 2/1970 | Koide et al. | 203/9 |
| 3,551,507 | 12/1970 | Sakuragi et al. | 203/9 |
| 3,681,202 | 8/1972 | Funkhouser | 203/53 |
| 3,775,493 | 11/1973 | De Simone et al. | 203/9 |
| 3,898,135 | 8/1975 | Tidwell et al. | 203/60 |
| 3,988,212 | 10/1976 | Watson | 203/9 |
| 4,081,332 | 3/1978 | Hein | 252/364 |

*Primary Examiner*—Wilbur L. Bascomb, Jr.
*Attorney, Agent, or Firm*—J. Hughes Powell, Jr.; Ernest K. Bean

[57] ABSTRACT

The separation of butadiene-1,3 from other C-4 hydrocarbons of lesser degree of unsaturation by extractive distillation with alkoxynitrile or aqueous alkoxynitrile as selective solvent is carried out with improved selectivity, without appreciable formation of butadiene-1,3 polymer and with consequent savings in energy by adding to the alkoxynitrile or aqueous alkoxynitrile an organic cosolvent which is dimethyl sulfoxide, sulfolane, butyrolactone, N-methyl pyrrolidone, morpholine, or trimethyl phosphate and/or an inhibitor which is 2,4-dinitrophenol or 2,4-dinitro-ortho-cresol. The organic cosolvent is present in the selective solvent composition in an amount of 5 to 30 percent by weight and the inhibitor in an amount of 0.05 to 0.6 percent by weight.

14 Claims, No Drawings

EXTRACTIVE DISTILLATION OF C-4 HYDROCARBONS USING MODIFIED ALKOXYNITRILE SOLVENT

BACKGROUND OF THE INVENTION

This invention relates to the separation and purification of C-4 hydrocarbons, particularly butadiene-1,3, from C-4 hydrocarbon mixtures utilizing extractive distillation with a selective solvent. It pertains to such extraction distillation when using an alkoxynitrile as a selective solvent component and is specifically directed to modifying the solvent composition as will be hereinafter described.

It is well known to the art that C-4 hydrocarbon mixtures containing C-4 hydrocarbons of different degrees of unsaturation, such as mixtures of butanes and butylenes or mixtures of butadiene-1,3 with butanes (including n-butane and isobutane) and butylenes (including butene-1, and cis- and trans-butene-2) which are not easily separable by ordinary fractional distillation because of similarities in boiling points and azeotrope formation are much more efficiently separated into their individual components by the process of extractive distillation with a solvent of relatively higher boiling point which selectively dissolves one or more of the more-unsaturated components. In the extractive distillation process as conventionally carried out, the selective solvent is introduced near the top of a distillation column and flows down the column as the distillation proceeds where it is contacted with the vapors of the hydrocarbons as they travel up the column. The more saturated hydrocarbons not dissolved by the solvent go overhead while the bottoms of the column contain the solvent plus the more unsaturated hydrocarbon components, which are removed from the solvent in a stripping column, or by other suitable means, and the lean solvent is recirculated to the column.

The choice of the selective solvent for use in the extractive distillation separation of butadiene-1,3 from C-4 hydrocarbon fractions of commercial availability (as from the dehydrogenation of butane or the oxydehydrogenation of butylenes or as a by-product of catalytic cracking of petroleum feedstocks such as naphtha to produce ethylene or propylene) has been the subject of intensive investigation for many years.

Acetone was one of the first proposed selective solvents but the first commercially practiced extractive distillation processes for separation of butadiene-1,3 from C-4 hydrocarbon streams used furfural, or a mixture of furfural with a smaller amount of water, as the selective solvent. Processes using other solvents for this purpose were subsequently developed; some of such other solvents of particular prominence include acetonitrile, (ACN), dimethyl formamide (DMF), dimethyl acetamide (DMA), and N-methyl pyrrolidone (NMP). The use of these solvents in place of furfural offered advantages in terms of selectivity but, unfortunately, they could not be substituted in commercial plants already on stream designed for use with furfural without extensive costly modification related to their different physical properties and lack of compatibility with the installed processing scheme.

This disadvantage in the commercial use in existing plants of selective solvents other than furfural is not so significant in the case of the use of an alkoxynitrile solvent, particularly 3-methoxy propionitrile (also known as beta-methoxy propionitrile) in accordance with U.S. Pat. No. 3,372,109. As disclosed therein 3-methoxy propionitrile (MOP) offers advantages over furfural in that it is less corrosive than furfural, more soluble in water which permits the use of greater quantities of water as co-solvent and more selective to the separation of butadiene-1,3 from butylenes.

However, as disclosed in U.S. Pat. No. 3,898,135, attempted practice on a commercial scale in a butadiene plant of the extractive distillation process using as the selective solvent MOP, or a mixture of MOP with water as co-solvent (as a substitute for the use of furfural or aqueous furfural) results in such serious disadvantages as to be entirely unpracticable. Fouling and plugging of equipment due to butadiene-1,3 polymerization are severe resulting in frequent shut downs of operations as well as losses of solvent and of butadiene-1,3 recoverable. The aforesaid U.S. Pat. No. 3,898,135 proposes to overcome these disadvantages by using a selective solvent composition comprising by weight 70 to 98% of alkoxynitrile, preferably MOP, 0.5 to 25% of furfural and 1 to 20% water.

The problem of preventing the polymerization of butadiene-1,3 during its extractive distillation separation from C-4 hydrocarbons fractions using selective solvents other than MOP, specifically DMF, DMA, NMP, ACN, and acetone, had previously been recognized in U.S. Pat. Nos. 3,309,412 and 3,551,507 and proposed therein to be ameliorated by including a small amount of furfural or benzaldehyde or any of a wide range of aromatic nitro compounds, including nitrophenol and dinitrophenol, in the solvent composition. Further, U.S. Pat. No. 3,681,202, directed to a means of effecting improved control and greater capacity in an extractive distillation tower for purification of C-4 or C-5 hydrocarbon streams by the expedient of removal of a side stream and premixing the side stream with the solvent externally of the tower, had previously disclosed that mixtures of acetone, ACN, dimethyl sulfoxide, furfural, NMP, methyl ethylketone, DMA, and MOP, with each other and with water, could be used as solvents for the extractive distillation. Despite these previous disclosures, however, the only known commercial process for the extractive distillation separation of butadiene-1,3 from C-4 hydrocarbon streams using MOP (or other alkoxynitrile) as a selective solvent component remains the process of the aforementioned U.S. Pat. No. 3,898,135 using as the selective solvent a mixture of MOP (or other alkoxynitrile) furfural and water.

The separation and purification of butadiene-1,3 from C-4 hydrocarbon streams using extractive distillation with a selective solvent is at best an energy intensive unit operation because of the necessity to use a large excess of solvent to facilitate the desired separation. Furthermore, the erection of new facilities for production of butadiene-1,3 of the high purity required for polymerization to synthetic rubbers (eg SBR, nitrile rubbers, cis-polybutadiene etc.) is not only quite costly but also complicated, and often impossible, due to environmental considerations. Consequently, there is an urgent need for a butadiene extractive purification process which can be used in existing plants designed for operation with a furfural containing solvent, in which the solvent composition used is more selective for butadiene-1,3 separation than furfural, in which the capacity of the extractive distillation unit to process the C-4 stream is increased, in which there are minimal difficulties due to polymerization of butadiene-1,3 to form a polymer which causes plugging and fouling of equipment, and in which the solvent composition used is completely furfural-free, thereby eliminating the formation of polymers from furfural (whether furfural—butadiene-1,3 adducts or other furfural polymers) and attendant loss of solvent in the "solvent clean-up" operation. In other words, modification of the process of U.S. Pat. No. 3,898,135 by use of a selective solvent composition which improves upon the selectivity of MOP (or other alkoxynitrile) but which overcomes the disadvantages due to the presence of furfural and enables the process to be more efficient and energy saving, is the specific objective of this invention as reflected by its background as hereinabove set forth.

SUMMARY OF THE INVENTION

This invention provides an extractive distillation process for separation and purification of butadiene-1,3 from C-4 hydrocarbon streams in which the selective solvent used is a composition comprising an alkoxynitrile of the formula $R_1$—O—$R_2$—CN wherein $R_1$ and $R_2$ are alkyl radicals of 1 to 5 carbon atoms, together if desired, and preferably, with water in an amount of 1 to 20 weight percent based on total weight of the composition, and additionally containing one or more other specific additives. The specific additives of this invention are limited to (1) another solvent (herein termed organic co-solvent) selected from the group consisting of dimethyl sulfoxide (DMSO), butyrolactone (BTL), N-methyl pyrrolidone (NMP), sulfolane, morpholine, and trimethyl phosphate (TMP) each of which, or a combination of which, in a concentration of 5 to 30 weight percent, preferably 10 to 30, of the composition, unpredictably increases the selectivity of the solvent composition thereby enabling savings in solvent and energy, while otherwise improving the operation of the process, and/or (2) a dinitro phenol inhibitor selected from the group consisting of 2,4-dinitrophenol (DNP) and 2,4-dinitro ortho cresol (DNC), each of which, or a combination of which, in only small concentrations, of the order of 1,500 ppm (0.15%), unpredictably prevents undesirable fouling and plugging of equipment due to polymer formation or otherwise, and decreases solvent loss and energy consumption without detracting from the selectivity of the solvent composition.

The preferred extractive distillation process of this invention efficiently separates butadiene-1,3 from C-4 hydrocarbon mixtures also containing n-butane, isobutane, butene-1, isobutene, trans-butene-2, and cis-butene-2, through the use of a selective solvent composition comprising by weight 50 to 95 percent of an alkoxynitrile, especially MOP, 1 to 20 percent water, 5 to 30 percent of an organic co-solvent of the group set forth above, especially DMS, and 0.05 to 0.06 percent (500 to 6,000 ppm) of an inhibitor of the group set forth above especially DNP.

Such solvent compositions are new compositions of matter and hence the invention in another aspect is directed thereto. They may be used not only as extractive distillation solvents for separation of butadiene-1,3 from C-4 hyrocarbon streams, but as solvents for other purposes such as for the separation of other aliphatic hydrocarbons of different degrees of saturation in other extractive distillation processes as in separation of isoprene from C-5 hydrocarbon streams, or in processes other than extractive distillation.

DETAILED DESCRIPTION OF INVENTION

The extractive distillation process of this invention is used to separate butadiene-1,3 from C-4 hydrocarbon streams using an alkoxynitrile as the main selective solvent component for the extractive distillation. It is an improvement over the process of U.S. Pat. No. 3,898,135 wherein extractive distillation of C-4 hydrocarbons is effected with a selective solvent composition containing alkoxynitrile, water and furfural, the improvement consisting of using with the alkoxynitrile in the selective solvent composition, in place of furfural, from 5 to 30 weight percent based on total solvent composition of one or more additives which are any of six specific organic co-solvents and/or a small amount of any of two specific inhibitors. Details concerning the improvements effected through the selection of the specific organic co-solvent additive and/or the inhibitor additive will be set forth hereinbelow after a description of the butadiene-1,3 containing C-4 hydrocarbon stream used in the process, the alkoxynitrile component of the selective solvent composition and the operation of the extractive distillation process.

C-4 Hydrocarbon Stream.

C-4 hydrocarbon streams containing appreciable proportions, of the order of at least about 20 mole percent, of butadiene-1,3 are derived from various sources as is well known to the art. One source is from the dehydrogenation or oxydehydrogenation of butane-butylene or butylene streams and another source is the by-product C-4 fraction from the pyrolysis of naphtha or other petroleum feedstocks under conditions to yield ethylene and/or propylene. In any event the C-4 hydrocarbon stream normally contains, in addition to butadiene-1,3 appreciable proportions, as great or greater than the proportion of butadiene-1,3, of various butylenes including n-butene-1, trans-butene-2, cis-butene-2, and isobutylene as well as smaller proportions of butanes including n-butane and isobutane. Additionally other C-4 hydrocarbons such as butyne-2 and vinyl acetylene may be present, generally only in trace amounts, as may hydrocarbons lower or higher than C-4 such as propane, propylene and neopentane. When the C-4 stream is the effluent from oxydehydrogenation of butylenes it is also possible that non-hydrocarbon gases such as hydrogen, nitrogen, CO and $CO_2$ can be present. Any of the above or other C-4 hydrocarbon streams may be subjected to the extractive distillation process of this invention. Usually and preferably, however, the invention is applied to C-4 hydrocarbon streams containing from 20 to 90 mole percent butadiene-1,3, from 5 to 30 mole percent butene-1, from 1 to 15 mole percent trans-butene-2, from 1 to 15 mole percent cis-butene-2, from 1 to 20 mole percent isobutylene, and from 1 to 15 mole percent butanes.

Alkoxynitrile Component of Selective Solvent Composition.

The alkoxynitrile component of the improved selective solvent compositions of this invention, as is well known from U.S. Pat. Nos. 3,436,437 and 3,895,138, is a compound of the formula $R_1$—O—$R_2$—CN wherein $R_1$ is an alkyl and $R_2$ is an alkylene radical each of which is preferably straight chain, but can also be branched chain, and contains from 1 to 3 carbon atoms. Specific alkoxynitriles are 3-methoxypropionitrile (MOP), which is most preferred, 3-ethoxypropionitrile (EOP), which is next preferred, 2-methoxyacetonitrile, 2-ethoxyacetonitrile, 3-methoxybutyronitrile, 4-methoxybutyronitrile, 4-propoxybutyronitrile, etc. and mixtures thereof. These alkoxynitriles are known from the above patents to dissolve butadiene-1,3 in preference to the less unsaturated butylenes and butanes. They are also known to be effective when admixed with 1 to about 25 weight by weight of water.

Operation of Extractive Distillation Process.

Processes for the extractive distillation of C-4 hydrocarbon streams are well known in the art and the operation thereof, considered apart from the selective solvent used therein, is not critical in this invention. The design and selection of equipment can be determined by those skilled in the art and the equipment present in existing commercial plants can be used in this invention without extensive modification. Conventional extractive distillation equipment may be used and may include baffle column, bubble trays, packed column, etc. The number of theoretical plates and the length and diameter of the column will depend on the flow rates and the degree of extraction desired and can be calculated by known methods.

Generally the process is carried out by introducing the C-4 hydrocarbon stream into the column at a point near or below the mid-point of the column and introducing the selective solvent composition above the point of entrance of the C-4 hydrocarbon feed preferably at or above the top one-third of the column. Temperature and pressure conditions are normally maintained such that the C-4 hydrocarbon feed is in vapor phase. The vapor phase contacts the liquid phase countercurrently and the butadiene-1,3 vapors are preferentially extraced into the liquid phase. The vapors taken off overhead of the column thus contain a proportionately greater amount of the more saturated C-4 hydrocarbon components while the solvent composition containing proportionately more butadiene-1,3 is taken off at the buttom as a liquid stream. The bottoms stream is fed to a stripper where the solvent composition is freed from the dissolved more unsaturated hydrocarbons and recycled to the extractive distillation column. There can be various arrangements of equipment for separation of the overhead into components and for treatment of the bottoms of the column. For example, there can be refluxes for part of the overhead, premixing of refluxes into the solvent, reboilers for the bottoms and removal of high boiling components from the solvent in a heavy ends column.

The temperature and pressure of the extractive distillation process will vary according to the particular C-4 hydrocarbon mixture being separated and the particular nature of the selective solvent composition but temperatures will generally be between 0° C. and 200° C. preferably in the range of 50° C. to 150° C., and pressures will range from atmospheric to 200 psig, but these are non-limiting pressure ranges since even sub-atmospheric pressures may in some instances be desirable.

The quantity of selective solvent composition will vary widely with the type of equipment and the desired efficiency of the separation but, in general, the quantity of solvent will range from about 1 to about 10 parts by weight to 1 weight part of the C-4 hydrocarbon feed. The column may be operated with reflux and the reflux ratio may be varied widely.

Selection of Organic Cosolvent Additive.

This invention provides a solvent composition which is more selective for the separation of butadiene-1,3 from butylenes than is MOP (or other alkoxynitrile) either alone or with water as cosolvent, and which can be used equally as well in existing commercial plant configurations designed to operate with furfural or aqueous furfural as the selective solvent. This is accomplished through use of a mixture of MOP (or other alkoxynitrile) with 5 to 30 weight percent based on total composition of any of six specific organic cosolvent additives. These are dimethyl sulfoxide (DMSO), butyrolactone (BTL), N-methyl pyrrolidone (NMP), sulfolane, morpholine, and trimethyl phosphate (TMP).

While U.S. Pat. No. 3,372,109 generally states that MOP can be used with a cosolvent, it specifically mentions only water as cosolvent and its disclosure reflects the inability of the art to predict utility, and selectivity for separation of butadiene-1,3 from butylenes, of any given substance, among the literally thousands of compounds and combinations thereof in existence. In view of this unpredictability the only known selective solvent composition containing MOP with any additive other than water is the MOP-furfural-water composition of U.S. Pat. No. 3,898,135, and in that case the presence of furfural actually decreases the selectivity of the solvent and is undesirable for the other reasons herein explained.

However, the selection of a suitable organic cosolvent for MOP to be used in an existing butadiene plant depends not only on the unpredictable selectivity for the butadiene-1,3/butylene separation but also on other factors possibly predictable from known characteristics such as compatability with carbon steel equipment and processing configuration used in the plant, thermal stability so as not to decompose during use, a boiling point substantially as high or higher than MOP but not so high as to increase reboiler fouling and require higher pressure steam in the stripper reboiler, a specific heat not so high as to increase energy consumption, a density such as to increase the density of the solvent mixture and increase the amount of solvent (in terms of weight) which can be circulated in the tower thereby increasing its capacity at a fixed ratio between solvent composition and C-4 stream and a viscosity sufficiently low as not decrease tray efficiency.

The selectivity of a solvent composition for the extractive distillation separation of butadiene-1,3 from butylenes, while unpredictable, can be determined by measuring the relative volatilities in the presence of the solvent composition of a mixture of the most difficultly separable C-4 hydrocarbon pairs in the C-4 hydrocarbon stream, ie, a mixture of butadiene-1,3 with trans-butene-2, which is the key pair, a mixture of butadiene-1,3 with cis-butene-2 and/or a mixture of butadiene-1,3 with butene-1. The "relative volatility" for the hydrocarbon pair in question is obtained by the equation:

$$\text{Relative volatility} = \frac{(A)/(B)}{(C)/(D)}$$

wherein (A) is the mole percent of the butene in the vapor phase, (B) is the mole percent of the butene in the liquid phase, (C) is the mole percent butadiene-1,3 in the vapor phase, and (D) is the mole percent butadiene-1,3 in the liquid phase. The higher the relative volatility the easier the separation of the key hydrocarbon pairs. Differences in relative volatility of as low as 0.01 are significant in an extractive distillation operation. Relative volatility of the key pair, trans-butene-2 and butadiene-1,3 at infinite dilution is known as the "maximum separation factor" (MaxSF) and can be determined rather rapidly by a gas chromatographic (G.C.) technique described by Tassios in Hydrocarbon Processing July 1970, pages 114 to 118, incorporated herein by reference. The higher the MaxSF of a given solvent composition the more selective it is for the extractive distillation separation of butadiene-1,3 from butylenes and if a given solvent composition has a MaxSF 2% or more higher than the solvent composition with which it is compared, the use of the given solvent composition substantially improves the solvent extractive distillation process.

The following examples present data demonstrating that the solvent compositions containing MOP with the organic cosolvents of this invention are substantial improvements over other solvent compositions containing MOP as a component.

EXAMPLE 1

CONTROL-MAXIMUM SEPARATION FACTORS OF KNOWN SELECTIVE SOLVENT COMPOSITIONS

In this Example the G.C. Technique is used to determine the MaxSF as between butadiene-1,3 and trans-butene-2 when using as selective solvents for extractive distillation (1) 95% furfural, 5% water as has been conventional in extractive distillation processes and for which many existing plants have been designed (2) 95% MOP, 5% water as taught by U.S. Pat. No. 3,436,437 and (3) a three component solvent composition containing MOP, water, and furfural as taught by U.S. Pat. No. 3,898,135.

The results are as set forth in Table I.

TABLE I

| Test No. | Solvent Composition (wt. %) | | | MaxSF at 40° C. |
|---|---|---|---|---|
| | % furfural | % MOP | % Water | |
| 1 | 95 | 0 | 5 | 1.521 |
| 2 | 20 | 75 | 5 | 1.669 |
| 3 | 15 | 80 | 5 | 1.678 |
| 4 | 10 | 85 | 5 | 1.689 |
| 5 | 5 | 90 | 5 | 1.698 |
| 6 | 0 | 95 | 5 | 1.708 |

It is apparent that in the solvent compositions containing furfural added to MOP as taught by U.S. Pat. No. 3,898,135 the furfural does not improve but rather decreases the selectivity of the MOP. The decrease in selectivity of 1.8% (Test No. 3 compared with Test No. 6) means in a large commercial butadiene plant an additional steam consumption costing from one-half to one million dollars per year at an energy cost of three dollars per MM BTU.

EXAMPLE 2

SELECTION OF ORGANIC COSOLVENT ADDITIVES OF THIS INVENTION

In this Example the GC technique is used to determine the MaxSF of a solvent composition containing aqueous MOP together with, as additives thereto, 20% by weight, based on the total solvent composition, of a wide variety of organic chemicals, many, but not all, of which are indicated by the patent literature to be useful otherwise than in combination with MOP in the extractive distillation separation of more unsaturated from more saturated hydrocarbons. The results are presented in Table II in which the right hand column notation "OK" indicates that the cosolvent in question possesses a combination of known physical properties which would enable it to be suitable as a solvent component in butadiene-1,3 separation from butylenes by the extractive distillation process as practiced in existing commerical plants, while the notation "NS" (not suitable) indicates that the cosolvent would not be suitable for the reasons indicated in the footnotes. No notation is present in this column for potential cosolvents for which MaxSF is lower or not significantly higher (less than 2% enhancement) than that for the control. Table II demonstrates that the five specific cosolvents of this invention for additives to aqueous MOP are unpredictably superior to other possible cosolvents.

TABLE II

VARIOUS ORGANIC COSOLVENTS FOR 95% AQUEOUS MOP
Solvent Composition = 75% MOP, 20% cosolvent, 5% water; Col t. = 20° C.

| Test No. | Cosolvent | MaxSF | % Increase MaxSF | Plant Use |
|---|---|---|---|---|
| 1 | 95% MOP, 5% water; no cosolvent control | 1.841[a] | — | — |
| 2 | DMSO | 1.932[b] | 4.9 | OK |
| 3 | Sulfolane | 1.947 | 5.8 | OK |
| 4 | NMP | 1.925 | 4.5 | OK |
| 5 | BTL | 1.880 | 2.1 | OK |
| 6 | TMP | 1.908 | 3.0[c] | OK |
| 7 | Morpholine | 1.918 | 3.5[c] | OK |
| 8 | N-acetyl morpholine | 1.960 | 6.5 | NS[d] |
| 9 | Triethylene glycol | 1.978 | 7.4 | NS[e] |
| 10 | Methoxy acetronitrile | 1.877 | 1.9 | NS[f] |
| 11 | Propylene carbonate | 1.868 | 1.5 | — |
| 12 | Methyl cyanoacetate | 1.835 | 0 | — |
| 13 | Dimethyl acetamide (DMA) | 1.833 | 0 | — |
| 14 | Dimethyl formamide (DMF) | 1.867 | 1.4 | — |
| 15 | Nitromethane | 1.846 | 0.3 | — |
| 16 | Propionitrile | 1.810 | 0 | — |
| 17 | Acetonitrile | 1.823 | 0 | — |
| 18 | Butyl cellosolve | 1.640 | 0 | — |
| 19 | Dimethyl malonate | 1.700 | 0 | — |
| 20 | Methyl cellosolve | 1.690 | 0 | — |
| 21 | Methyl carbitol | 1.720 | 0 | — |
| 22 | Ethylene glycol mono-ethyl ether | 1.670 | 0 | — |
| 23 | Dimethyl malonate | 1.753 | 0 | — |
| 24 | Methyl acetoacetate | 1.723 | 0 | — |
| 25 | Dimethyl carbonate | 1.775 | 0 | — |
| 26 | N-methyl morpholine | 1.760 | 0 | — |
| 27 | Valeronitrile | 1.765 | 0 | — |
| 28 | Triethyl phosphate | 1.788 | 0 | — |
| 29 | N-N-dimethyl propionamide | 1.812 | 0 | — |
| 30 | N, N-dibutyl propionamide | 1.726 | 0 | — |
| 31 | N-formyl piperidine | 1.850 | 0[g] | — |
| 32 | Butyronitrile | 1.748 | 0 | — |
| 33 | 3,4-Dimethyl thiazole | 1.762 | 0 | — |
| 34 | 2-Methyl imidazole | 1.875 | 1.2 | — |
| 35 | 3-Methyl piperdine | 1.754 | 0 | — |
| 36 | 3-cyclohexene-1-carbonitrile (acrylonitrile-butadiene adduct) | 1.765 | 0.6[h] | — |

Notes:
[a] average of 4 tests.
[b] average of 2 tests.
[c] proper control MaxSF is 1.853 based on average of 3 tests instead of control in Test 1.
[d] NS because no increase in MaxSF at 10% concentration, because results at 20% concentration possibly unreliable due to poor peak separation and because of tendency of cosolvent to decompose.
[e] NS because of combination of high boiling point, high specific heat and low thermal stability.
[f] NS as cosolvent because boiling point is too low (118° C. compared to 161° C. for MOP) and increase in MaxSF is marginal.
[g] proper control is 1.853 MaxSF.
[h] 10% cosolvent-control is 1.755 MaxSF.

Notes: (a) average of 4 tests (b) average of 2 tests (c) proper control MaxSF is 1.835 based on average of 3 tests instead of control in Test 1 (d) NS because no increase in MaxSF at 10% concentration, because results at 20% concentration possibly unreliable due to poor peak separation and because of tendency to cosolvent to decompose (e) NS because of combination of high boiling point, high specific heat and low thermal stability (f) NS as cosolvent because boiling point is too low (118° C. compared to 161° C. for MOP) and increase in MaxSF is marginal (g) proper control is 1.853 MaxSF (h) 10% cosolvent-control is 1.755 MaxSF.

EXAMPLE 3

VARIATION IN COSOLVENT CONCENTRATION

The procedure of Example 2 is used to demonstrate the improvement in MaxSF through the use of the specific cosolvents of this invention other than TMP (which is less preferred due to its unavailability and cost) in concentrations varying from 10 to 30 weight percent of the solvent composition. At 50% concentration MaxSF is still improved; however, the use of such a high concentration of cosolvent is not suitable in existing plants. The results are presented in Table III.

TABLE III

EFFECT OF COSOLVENT CONCENTRATION ON SOLVENT SELECTIVITY

| Test No. | Cosolvent | Cosolvent Concentration % weight | MaxSF | % Increase MaxSF |
|---|---|---|---|---|
| 1 | DMSO | 10 | 1.904 | 3.4 |
| 2 | DMSO | 20 | 1.932 | 4.9 |
| 3 | DMSO | 30 | 2.032 | 9.9 |
| 4 | Sulfolane | 10 | 1.555 | 0.8 |
| 5 | Sulfolane | 20 | 1.947 | 5.8 |
| 6 | Sulfolane | 30 | 2.015 | 9.5 |
| 7 | BTL | 10 | 1.890 | 2.7 |
| 8 | BTL | 20 | 1.880 | 2.1 |
| 9 | BTL | 30 | 1.914 | 4.0 |
| 10 | NMP | 10 | 1.876 | 1.9 |
| 11 | NMP | 20 | 1.924 | 4.5 |
| 12 | NMP | 30 | 1.915 | 4.0 |
| 13 | Morpholine | 10 | 1.862 | 0.5 |
| 14 | Morpholine | 20 | 1.918 | 3.5 |
| 15 | Morpholine | 30 | 1.886 | 1.8 |

EXAMPLE 4

This Example is submitted to show the increase in relative volatility of a C-4 hydrocarbon feed stream containing trans-butene-2, cis-butene-2, butene-1, and butadiene-1,3 when organic cosolvent additives of this invention are present in aqueous MOP. A modified Othmer still is used to arrive at the relative volatility data. The ratio of solvent composition to C-4 hydrocarbon feed is 9–10 parts by weight of solvent composition to one part by weight of the hydrocarbon feed. The contents of the still are boiled and the vapors are condensed and returned to the still as liquid. The still is allowed to come to equilibrium for about 3 hours. Samples of the liquid in the still and the condensed vapors are taken simultaneously and analyzed by gas chromatography. From the analyses the relative volatility for the butadiene-1,3 (BD) pair with each of cis-butene-2 (CB2), trans-butene-2 (TB2) and butene-1 (B1) is calculated and shown in Table IV.

TABLE IV

| Run No. (average of 3) | Solvent Composition | Pressure psig | Temp. °F. | Relative Volatility Data TB2/BD | CB2/BD | B1/BD |
|---|---|---|---|---|---|---|
| 1 | MOP-95%; H$_2$O-5%; (control) | 23 | 125 | 1.717 | 1.744 | 2.143 |
| 2 | MOP-75%; DMSO-20%; H$_2$O-5% | 19 | 125 | 2.53 | 1.82 | 3.43 |
| 3 | 95%-DMSO; H$_2$O-5% | 47 | 122 | 2.32 | 1.57 | 3.35 |
| 4 | MOP-75%; Sulfolane-20%; H$_2$O-5% | 23 | 125 | 2.29 | 1.76 | 3.04 |
| 5 | MOP-75%; BTL-20%; H$_2$O-5% | 25 | 124 | 1.748 | 1.646 | 2.456 |
| 6 | MOP-75%; NMP-20%; H$_2$O-5% | 19 | 125 | 1.94 | 1.43 | 2.51 |

It will be noted from Table IV that each of the organic cosolvents used resulted in a more selective solvent composition for each of the three C-4 pairs; and that the combination of 75% MOP and 20% DMSO with 5% water is more selective than either MOP or DMSO with the same amount of water.

Selection of Inhibitor

As indicated hereinabove the use of alkoxynitrile or aqueous alkoxynitrile as a selective solvent for the separation of butadiene-1,3 from C-4 hydrocarbon streams is unsatisfactory because of the high degree of fouling in the equipment due to polymerization of butadiene-1,3 at the operating temperatures require. The only known means of alleviating this is through the addition of furfural to the solvent but the presence of furfural not only reduces selectivity, but also is itself polymerizable and forms adducts with butadiene-1,3 which complicates solvent clean up and imposes a severe economic penalty on the operation.

This invention eliminates the polymer formation accompanying the use of alkoxynitrile solvent through inclusion in the alkoxynitrile solvent of a small amount of 2,4-dinitrophenol (DNP) or 4,6-dinitro-o-cresol (DNC). Although many substances are known to inhibit butadiene-1,3 polymerization, only these two specific inhibitors have been found to inhibit polymer formation during the elevated temperatures of the extractive distillation purification of butadiene-1,3 using MOP or other alkoxynitrile in the selective solvent. The advantages of using DNP or DNC are shown in the following Examples.

EXAMPLE 5

The following experimental technique is used to evaluate inhibitors for butadiene-1,3 in MOP solvent. Four hundred grams of the solvent composition containing the inhibitor are charged to a carbon steel cylinder. Twenty-five grams of carbon steel chips are added to provide additional surface area for fouling. The cylinder is purged with nitrogen, partially evacuated and liquid butadiene-1,3 (which has been distilled under nitrogen to remove impurities which may have been present) is injected into the cylinder. The cylinder is weighed to determine the exact amount of butadiene-1,3 charged-normally about 65 to 68 grams. The cylinder is then placed in an oil bath maintained at 295° F. for 48 hours. The cylinder is removed from the oil bath, cooled and reweighed to determine if any butadiene-1,3 is lost. Its contents are then filtered. The material remaining on the filter paper is dried in a vacuum over and weighed. This is a portion of the insoluble polymer, called (A). The filtered solvent-butadiene-1,3 mixture is distilled under vacuum and the material remaining in the pot is coagulated with methanol, washed and dried in a vacuum oven and weighed. This is the soluble polymer called (B). The carbon steel cylinder is then filled with toluene and held in an oil bath for 24–48 hours at 295° F. whereby polymer sticking to the sides of the cylinder and to the chips is dissolved in toluene. After distilling off the toluene under vacuum the residual polymer is coagulated with methanol, filtered, washed, dried and weighed. This material called (C), plus (A) is regarded as the insoluble polymer and (B) is regarded as the soluble polymer. Total polymer formation is the sum of (A), (B), and (C). The polymer formed is expressed as a percentage of the initial content of butadiene-1,3. Table V shows results when using various inhibitors at various concentrations together with MOP in the solvent composition. It is apparent from the data that DNP and DNC are as effective inhibitors in small concentrations as is furfural at the 15% by weight concentration. It is also indicated that DNP and DNC are unique among commercially available nitrogen containing inhibitors.

TABLE V
VARIOUS INHIBITORS IN MOP SOLVENT

| Test No. | Solvent Composition Weight % | % Polymer Based on BD Content | | |
|---|---|---|---|---|
| | | Soluble (B) | Insoluble (A+C) | Total (A+B+C) |
| 1 | 95 MOP; 5 $H_2O$ No inhibitor | — | — | 10.0 |
| 2 | 95 MOP; 5 $H_2O$ 5 furfural | 0 | 5.77 | 5.77 |
| 3 | 85 MOP; 5 $H_2O$ 10 furfural | 0.03 | 2.06 | 2.09 |
| 4 | 80 MOP; 5 $H_2O$ 15 furfural | 0 | 0.83 | 0.83 |
| 5 | 95 MOP; 5 $H_2O$ 2000 ppm DNP | 0.13 | 0.52 | 0.65 |
| 6 | 95 MOP; 5 $H_2O$ 1500 ppm DNC | 0.03 | 0.67 | 0.70 |
| 7 | 95 MOP; 5 $H_2O$ 2000 ppm NPH* | 0.32 | 5.02 | 5.34 |
| 8 | 95 MOP; 5 $H_2O$ 2000 ppm DEHA** | 0.12 | 12.58 | 12.70 |

*NPH is N-nitroso phenyl hydroxyl amine
**DEHA is N,N-diethyl hydroxylamine, known in the trade as "Pennstop 1886".

EXAMPLE 6

The experimental technique of Example 5 is repeated except that the heat treatment is varied at 250° F., 295° F., and 345° F. DNP or DNC is the inhibitor and is present in 95% aqueous MOP. The data set forth in Table VI shows that DNP and DNC are effective inhibitors over a wide range of temperatures when present in small concentration of the order of 0.05 to 0.25% by weight (500 to 2,500 ppm) and that no more than about 0.2% by weight is needed.

TABLE VI

| Test No. | Inhibitor | Conc (ppm) | Temp °F. | % Polymer Based on BD Content | | |
|---|---|---|---|---|---|---|
| | | | | soluble (B) | insoluble (A+C) | total (A+B+C) |
| 1 | DNP | 0 | 250 | 0.06 | 3.79 | 3.85 |
| 2 | DNP | 500 | 250 | 0.11 | 0.98 | 1.09 |
| 3 | DNP | 1,000 | 250 | 0 | 0.78 | 0.78 |
| 4 | DNP | 1,500 | 250 | 0 | 0.33 | 0.33 |
| 5 | DNP | 500 | 295 | 0.48 | 2.90 | 3.38 |
| 6 | DNP | 1,000 | 295 | 0.11 | 0.73 | 0.84 |
| 7 | DNP | 1,500 | 295 | 0.10 | 0.41 | 0.51 |
| 8 | DNP | 2,500 | 295 | 0.09 | 0.33 | 0.42 |
| 9 | DNP | 0 | 345 | 0 | 3.70 | 3.70 |
| 10 | DNP | 1,000 | 345 | 0 | 1.38 | 1.38 |
| 11 | DNP | 2,000 | 345 | 0 | 0.84 | 0.84 |
| 12 | DNC | 1,000 | 295 | 0 | 1.20 | 1.20 |
| 13 | DNC | 1,500 | 295 | 0 | 0.10 | 0.10 |
| 14 | DNC | 2,000 | 295 | 0 | 0.06 | 0.06 |

EXAMPLE 7

This Example illustrates that the inhibitor additives of this invention are effective when used in combination with the organic cosolvents of this invention. The experimental technique of Example 5 is again repeated except the amount of butadiene-1,3 charged is decreased from about 60 to about 40 grams and the heat treatment is carried out for 48 hours at 316° F. DMSO and sulfolane are selected as representative of the specific organic cosolvents of this invention and are used in a solvent composition containing 75% MOP, 5% $H_2O$, 20% of the organic cosolvent, and the indicated amount of DNP or DNC. The results are shown in Table VII. Runs 7 and 14 using no inhibitor represent controls.

TABLE VII

| Test No. | Co-solvent | Inhib-itor | Inhibitor Conc. (ppm) | % Polymer Based on Bd Content | | |
|---|---|---|---|---|---|---|
| | | | | soluble (B) | insoluble (A+C) | total (A+B+C) |
| 1 | DMSO | DNP | 1,500 | 0 | 2.73 | 2.73 |
| 2 | DMSO | DNP | 3,000 | 1.28 | 1.20 | 2.48 |
| 3 | DMSO | DNP | 6,000 | 0.95 | 4.80 | 5.75 |
| 4 | DMSO | DNC | 1,500 | 0.26 | 2.84 | 3.10 |
| 5 | DMSO | DNC | 3,000 | 1.70 | 2.07 | 3.77 |
| 6 | DMSO | DNC | 6,000 | 1.15 | 2.92 | 4.10 |
| 7 | DMSO | None | — | 0.7 | 18.3 | 19.0 |
| 8 | Sulfolane | DNP | 1,500 | 1.40 | 2.02 | 3.42 |
| 9 | Sulfolane | DNP | 3,000 | 2.69 | 2.13 | 4.82 |
| 10 | Sulfolane | DNP | 6,000 | 2.53 | 1.73 | 4.26 |
| 11 | Sulfolane | DNC | 1,500 | 1.10 | 1.30 | 2.40 |
| 12 | Sulfolane | DNC | 3,000 | 0.36 | 1.36 | 1.72 |
| 13 | Sulfolane | DNC | 6,000 | 1.13 | 1.20 | 2.33 |
| 14 | Sulfolane | None | — | 0.3 | 8.2 | 8.5 |

Preferred Solvent Compositions

The above detailed descriptions and data establish that improved selectivity in the extractive-distillation separation of butadiene-1,3 from C-4 hydrocarbon streams containing difficultly separable butenes can be effected while at the same time preventing undesirable fouling of the equipment due to butadiene-1,3 polymer formation by using as the selective solvent a composition containing MOP or other alkoxynitrile (2) water (3) an organic cosolvent additive which is DMSO, sulfolane, BTL, NMP, morpholine, or TMP and (4) an inhibitor additive which is DNP or DNC, in concentrations by weight of 50 to 94 or 95% of (1); 1 to 20% of (2); 5 to 30% preferably 10 to 30% of (3); and 0.05 to 0.6% of (4). The following Example 8 illustrates such a separation and summarizes the advantages thereof.

EXAMPLE 8

A two-inch diameter stainless steel extractive distillation column with 95 seive trays and a tray spacing of 1.875 inches is used to separate a mixture of C-4 hydrocarbons containing about 43% butadiene-1,3, 20% butene-1, 4% cis-butene-2, 6% trans-butene-2, 24% isobutene, 2% n-butane, 1% isobutane and 0.1% vinyl acetylene and methyl acetylene. This C-4 hydrocarbon feed is introduced into the column below its mid-point on tray no. 35 (counting from the bottom) at a rate of 5 to 8 grams per minute. An extractive distillation solvent compositon containing 75% MOP, 5% water, and 20% DMSO, in which is dissolved 1,500 ppm of DNP, is introduced into the column at a point near the top of the column on tray no. 90 (from the bottom) at a rate of 35 to 40 grams per minute. Thus the solvent composition to C-4 ratio varies from 5 to 8 (wt/wt). The top of the column is maintained at a temperature of about 130° F. and a pressure of about 80 psia while the bottom of the column is maintained at a temperature of about 230°-240° F. and a pressure of about 81 psia. A C-4 distillate stream, which is lean in butadiene-1,3, is taken from the top of the column and from the overhead stream a reflux stream is returned to the top of the column with a reflux ratio of 3.0 and a temperature of about 65° C. The liquid stream taken from the bottom of the column consisting of solvent composition and dissolved C-4 hydrocarbons, which is rich in butadiene-1,3 is passed through a stripping column where the butadiene-1,3 is separated by distillation and the lean solvent recycled to the column.

The column is operated continuously for 571 hours during which time the distillate and bottom streams are periodically analyzed. The "rejection" of paraffins (butane and isobutane) and olefins (butene-1 cis and trans-butene-2 and isobutene) in the distillate stream and the "recovery" of butadiene-1,3 in the bottom is determined by calculating a material balance around the column. The "rejection" of a component (or components) in the distillate stream is defined as the amount of that component in the distillate divided by the amount of that component in the C-4 feed stream multiplied by 100. Similarily the "recovery" of butadiene-1,3 in the bottom stream is defined as the amount of butadiene-1,3 in the bottom stream divided by the amount of butadiene-1,3 in the C-4 feed stream multiplied by 100.

The data taken shows that when there is 99% "recovery" of butadiene-1,3 in the bottom stream the olefin "rejection" in the distillate stream is 51% at a solvent to C-4 hydrocarbon ratio (wt/wt) of 6.6 and is 53% at the ratio of 6.9.

In a control run carried out exactly as described above except that the solvent composition does not contain DMSO (ie it is 95% MOP, 5% water and contains DNP) at 99% "recovery" of butadiene-1,3 in the bottom stream the olefin "rejection" in the distillate stream is 48% at a solvent to C-4 hydrocarbon ratio of 6.6 and 51% at a ratio of 6.9. This demonstrates an improvement, which is quite significant, of about 3% in the olefin "rejection" due to presence of the cosolvent and an increase in column capacity for C-4 streams of about 5% or, for the same capacity, a decrease in energy used of about 5% since most of the energy consumed is due to the sensible heat of the circulatory solvent.

In the above runs, in both of which DNP inhibitor is present in the solvent composition during the entire 531 hours operation there was no indication whatsoever of column fouling due to polymer formation, thus demonstrating the effectiveness of the DNP inhibitor under actual operating conditions.

I claim:

1. In an extractive-distillation process for separating butadiene-1,3 from a C-4 hydrocarbon stream containing C-4 hydrocarbons more saturated than butadiene-1,3 which process includes the steps of (a) introducing a selective solvent to an extractive distillation column (b) introducing said C-4 hydrocarbon stream to said column at a point below the point of introduction of said selective solvent (c) selectively extracting butadiene-1,3 from said C-4 hydrocarbon stream to form a liquid solvent fraction richer in butadiene-1,3 (d) withdrawing overhead from said column a vaporous C-4 hydrocarbon fraction richer in hydrocarbons less saturated than butadiene-1,3 (e) withdrawing said liquid solvent fraction richer in butadiene-1,3 from the bottom of said column (f) introducing said withdrawn liquid solvent fraction to a stripping column to remove said butadiene-1,3 and (g) recycling the lean solvent to said extractive distillation column, and in which process the selective solvent contains an alkoxynitrile of the structure $R_1-O-R_2-CN$ wherein $R_1$ is an alkyl group and $R_2$ is an alkylene group each containing from 1 to 3 carbon atoms, the improvement which consists of adding to the selective solvent an organic cosolvent selected from the class consisting of dimethyl sulfoxide, sulfolane, butyrolactone, N-methyl pyrrolidone, morpholine and trimethyl phosphate in an amount from 5 to 30 percent by weight of the total solvent and/or an inhibitor selected from the class consisting of 2,4-dinitrophenol and 2,4 dinitro-ortho-cresol in an amount from 0.05 to 0.6 percent by weight of the total solvent.

2. The process improvement of claim 1 wherein the alkoxynitrile is 3-methoxy propionitrile.

3. The process improvement of claim 2 wherein the solvent additionally contains water in an amount from 1 to 20 percent by weight of the total solvent.

4. The process improvement of claim 2 wherein the inhibitor is 2,4 dinitrophenol.

5. The process improvement of claim 2 wherein the organic cosolvent is dimethyl sulfoxide.

6. The process improvement of claim 1 wherein the selective solvent consists by weight of 50 to 95 percent of alkoxynitrile, from 1 to 20 percent water, from 10 to 30 percent of organic cosolvent and from 0.05 to 0.6 percent inhibitor.

7. The process improvement of claim 6 wherein the alkoxynitrile is 3-methoxy propionitrile.

8. The process improvement of claim 7 wherein the organic cosolvent is dimethyl sulfoxide.

9. The process improvement of claim 7 wherein the organic cosolvent is sulfolane.

10. The process improvement of claim 6 wherein the inhibitor is 2,4-dinitrophenol.

11. A solvent composition for separating mixtures of hydrocarbons of varying degrees of unsaturation consisting of 40 to 95 weight percent of an alkoxynitrile of the formula $R_1-O-R_2-CN$ wherein $R_1$ is alkyl and $R_2$ is alkylene each containing from 1 to 3 carbon atoms, 1 to 20 weight percent water, 5 to 30 weight percent of an organic cosolvent selected from the class consisting of dimethyl sulfoxide, sulfolane, butyrolactone, N-methyl pyrrolidone, morpholine and trimethyl phosphate and form 0.05 to 0.6 weight percent of an inhibitor selected from the class consisting of 2,4-dinitrophenol and 2,4-dinitro-ortho-cresol.

12. The composition of claim 11 wherein the alkoxynitrile is 3-methoxy propionitrile.

13. The composition of claim 12 wherein the organic cosolvent is dimethyl sulfoxide.

14. The composition of claim 13 wherein the inhibitor is 2,4-dinitro-phenol.

* * * * *